US 6,675,798 B1

(12) United States Patent
Tyomkin et al.

(10) Patent No.: US 6,675,798 B1
(45) Date of Patent: Jan. 13, 2004

(54) AUTOMATICALLY REGULATING OXYGEN FLOW TO A PATIENT

(75) Inventors: Tatyana Tyomkin, Tirat HaCarmel (IL); Evgeny Tyomkin, Ashdod (IL)

(73) Assignee: AutoMed - Automatic Dosage Systems, Ltd., Ashdod (IL)

( * ) Notice: Subject to any disclaimer, the term of this patent is extended or adjusted under 35 U.S.C. 154(b) by 375 days.

(21) Appl. No.: 09/761,669

(22) Filed: Jan. 18, 2001

(51) Int. Cl.[7] .............................................. A61M 16/00
(52) U.S. Cl. .............................. 128/204.23; 128/204.18
(58) Field of Search ..................... 128/200.24, 204.18, 128/204.21, 204.22, 204.23, 204.26, 204.29, 205.11, 205.22, 205.24; 600/323–325, 326, 328, 529, 533, 535, 538

(56) References Cited

U.S. PATENT DOCUMENTS

| | | | | |
|---|---|---|---|---|
| 4,020,834 A | * | 5/1977 | Bird ....................... | 128/204.25 |
| 4,519,387 A | * | 5/1985 | Durkan et al. .......... | 128/204.23 |
| 4,584,996 A | * | 4/1986 | Blum ..................... | 128/204.21 |
| 4,706,664 A | * | 11/1987 | Snook et al. ........... | 128/204.23 |
| 4,883,050 A | * | 11/1989 | Urman et al. .......... | 128/202.27 |
| 4,971,049 A | * | 11/1990 | Rotariu et al. ......... | 128/204.21 |
| 5,103,814 A | * | 4/1992 | Maher .................... | 128/204.18 |
| 5,239,994 A | * | 8/1993 | Atkins .................... | 128/204.18 |
| 5,320,093 A | * | 6/1994 | Raemer .................. | 128/203.12 |
| 5,329,931 A | | 7/1994 | Clauson et al. | |
| 5,365,922 A | | 11/1994 | Raemer | |
| 5,423,327 A | | 6/1995 | Clauson et al. | |
| 5,558,086 A | * | 9/1996 | Smith et al. ........... | 128/204.26 |
| 5,626,131 A | | 5/1997 | Chua et al. | |
| 5,634,461 A | * | 6/1997 | Faithfull et al. ............ | 600/483 |
| 5,682,877 A | * | 11/1997 | Mondry .................. | 128/204.23 |
| 5,697,364 A | | 12/1997 | Chua et al. | |
| 5,735,268 A | | 4/1998 | Chua et al. | |
| 5,738,090 A | * | 4/1998 | Lachmann et al. ..... | 128/204.23 |
| 5,752,506 A | * | 5/1998 | Richardson ............ | 128/204.18 |
| 5,810,759 A | * | 9/1998 | Merz ........................ | 604/6.11 |
| 5,865,174 A | * | 2/1999 | Kloeppel ................ | 128/204.23 |
| 5,887,611 A | * | 3/1999 | Lampotang et al. ........... | 137/93 |
| 5,934,277 A | * | 8/1999 | Mortz ........................ | 600/323 |
| 6,186,142 B1 | * | 2/2001 | Schmidt et al. ........ | 128/204.23 |
| 6,196,222 B1 | * | 3/2001 | Heinonen et al. ....... | 128/204.23 |
| 6,220,244 B1 | * | 4/2001 | McLaughlin ........... | 128/204.23 |
| 6,360,745 B1 | * | 3/2002 | Wallace et al. ........ | 128/204.21 |
| 6,371,114 B1 | * | 4/2002 | Schmidt et al. ........ | 128/204.23 |
| 6,439,228 B1 | * | 8/2002 | Hete et al. .............. | 128/200.26 |
| 6,470,885 B1 | * | 10/2002 | Blue et al. .............. | 128/204.18 |
| 6,532,958 B1 | * | 3/2003 | Buan et al. ............. | 128/204.23 |

* cited by examiner

Primary Examiner—Weilun Lo
Assistant Examiner—Teena Mitchell
(74) Attorney, Agent, or Firm—Nixon & Vanderhye P.C.

(57) ABSTRACT

Automatically regulating oxygen flow to a patient, sympathetic to a patient's changing needs, is disclosed by a method and apparatus for providing a regulated flow of gas from a gas supply to increase or maintain the oxygen concentration in the patient's bloodstream; by measuring the concentration of the oxygen in the patient's bloodstream; by producing a signal indicative of the oxygen level; and by comparing the measured concentration of oxygen with a preset level, the flow of gas to the patient is constantly regulated. Additionally, in response to a gas flow failure to the patient, a flow of gas is maintained by initiating a flow of gas from an auxiliary gas supply.

14 Claims, 3 Drawing Sheets

AUTOMATICALLY REGULATING OXYGEN FLOW TO A PATIENT

FIELD OF THE INVENTION

The present invention generally relates to regulating the flow of a gas to a patient.

BACKGROUND OF THE INVENTION

Inhalation of oxygen, oxygen enriched air and a variety of other gases, vapors and liquid mists (aerosols) is a well-established treatment and well known in the art. Commonly, oxygen administration is carried out in hospital and other medical facility environments. This treatment has been extended to use in the home and other non-medical environments. Generally, at the outset, oxygen administration is carried out under professional medical supervision. In chronic or extended treatment cases, once the therapy has been established, continuous medical supervision is not required and patients use oxygen therapy outside the hospital environment, permitting them to lead active productive lives. Examples of such instances include patients suffering from chronic bronchitis, asthma, emphysema, occupational lung diseases and other lung associated conditions as well as cases involving breathing difficulty due to physical conditions, such as broken ribs and the like.

However, such long term oxygen therapy is generally carried out with a fixed prescribed flow rate, irrespective of a patient's changing needs during the course of a day. For example, a patient requires less oxygen while lying or asleep than when physically active. During the course of a day, a patient may have a change of circumstances, which would require a variation in oxygen flow rate.

A widely used primary portable supply of oxygen is a high-pressure metal cylinder. Where a patient has such a cylinder of oxygen, exhaustion of that cylinder represents a hazard especially to patients incapable of connecting another, spare cylinder. Recently, alternative oxygen generating devices have been developed. These are portable, light and may be positioned wherever the patient desires. Oxygen generators are electrically operated, draw air from the local environment and reduce the nitrogen content of the air to produce an oxygen rich mixture. There is, however, a significant potential hazard. In the event of a power failure and subsequent oxygen supply failure, it is necessary to have a back-up cylinder of oxygen, which must be manually connected to the patient's inhaler.

Within the scope of determining the blood oxygen level of a patient, generally, non-invasive blood oxygen measuring devices are preferred to invasive devices. An example of an invasive device is the so-called blood oxygen machine. However, a commonly utilized non-invasive device, called an oximeter, is used for measuring the level of oxygen in the bloodstream. This non-invasive instrument includes a fastening device, a Light Emitting Diode (LED) and a photodiode. This device emits a signal, which is a function of the oxygen level of the bloodstream. In addition, it sends out a pulse rate signal. Alternative devices include electrochemical, paramagnetic or laser absorption detection and the quenching of luminescence from a metalloporphyrin supply. The desirable physical characteristics of such a sensor include that it be small, robust with respect to environmental perturbations, and have a fast response time.

There is a need in the art, insofar as no provision is generally made, to monitor the patient's blood oxygen level so as to give an indication of the flow rate of oxygen required to maintain a desired blood oxygen level in the patient. Furthermore, no provision is generally made to effect replacement of a failed or exhausted primary oxygen supply to the patient without having to resort to manually connecting an alternative supply.

SUMMARY OF THE INVENTION

Generally, a patient undergoing oxygen therapy is prescribed a flow rate of oxygen by a medical professional. However, in many chronically ill patients, outside of hospitals there is little or no supervision by medically qualified personnel.

The present invention largely eliminates the need for constant supervision and provides a method and apparatus for controlling an appropriate flow of oxygen, sympathetic to a patient's changing needs. The technique includes measuring the concentration of oxygen in a patient's bloodstream and comparing this measurement with a desired level of oxygen. Using this comparison, the flow of oxygen to the patient is constantly regulated to optimally maintain the blood oxygen level at the desired level. This is an ongoing process so that any change in the patient's situation and consequent change in blood oxygen level will be compensated for, by a controlled change in the oxygen flow rate.

The present invention aims to control a flow of oxygen to a patient, responsive to a metric of the oxygen level in the patient's bloodstream. The present invention makes operating an oxygen inhalation system largely independent of medical supervision and the patient less dependent on assistance. Moreover, the present invention provides a solution to the problem of failure of gas flow from the primary oxygen supply by automatically initiating a replacement flow from an auxiliary emergency supply.

According to a preferred embodiment of the present invention, there is provided a method for controlling a flow of gas from a gas supply to a patient, the method including the following steps:

One) providing a regulated flow of a predetermined gas from a gas supply to a patient so as to increase the concentration in the patient's bloodstream of a preselected dissolved substance;

Two) measuring the concentration of the preselected dissolved substance in the patient's bloodstream;

Three) producing an output signal indicative of the measured concentration; and

Four) comparing the measured concentration of the preselected dissolved substance with a desired concentration thereof, so as to determine sufficiency of the regulated flow of the predetermined gas to the patient, and adjusting the regulated flow in accordance therewith.

According to a first preferred embodiment of the present invention, there is, in response to a failure of the flow of the predetermined gas, the additional step of initiating a flow of a predetermined gas from an auxiliary gas supply, thereby to maintain a flow of gas to the patient. This step occurs in response to a failure of the step of providing a regulated flow of a predetermined gas from a gas supply to a patient.

According to a variation of the first embodiment of the present invention, the additional step of initiating a flow of gas includes the sub-step of detecting a failure of the regulated gas flow from the gas supply below a predetermined gas flow.

According to a second embodiment of the present invention, the step of comparing the measured concentration of the preselected dissolved substance with the desired concentration includes the additional step of assigning, prior to the step of measuring the concentration of the preselected dissolved substance in the patient's bloodstream, at least one of the following:

One) a maximum desired concentration of the preselected dissolved substance in the patient's bloodstream; and Two) a minimum desired concentration of the preselected dissolved substance in the patient's bloodstream.

According to a third embodiment of the present invention, in the step of providing a regulated flow of a predetermined gas from a gas supply to a patient and the step of measuring a concentration of the preselected dissolved substance, the preselected dissolved substance is oxygen.

According to a fourth embodiment of the present invention, the step of measuring the concentration of the preselected dissolved substance in the patient's blood stream may be either invasive or non-invasive measuring.

According to a fifth embodiment of the present invention, in the step of providing a regulated flow of a predetermined gas, the predetermined gas contains oxygen.

Additionally, according to a sixth embodiment of the present invention, in the step of providing a regulated flow of a predetermined gas, the predetermined gas is substantially oxygen.

In accordance with another preferred embodiment of the present invention, there is provided apparatus for controlling a flow of gas from a gas supply to a patient, which includes:

One) a regulating valve arranged in association with a gas supply, for regulating a flow of gas therefrom to a patient in response to predetermined control signals;

Two) a sensor for measuring a concentration of a preselected dissolved substance in the blood stream of the patient and for providing an output signal indicative of the concentration of the measured substance;

Three) input apparatus for inputting a desired concentration of the dissolved substance in the patient's bloodstream; and Four) comparator apparatus associated with the automatic regulating valve, the sensor and the input apparatus, operative to compare a measured concentration with the desired concentration so as to determine sufficiency of the regulated flow of the predetermined gas to the patient, and so as to provide to the regulating valve a control signal so as to adjust the regulating valve in accordance with the determined sufficiency of the regulated flow.

According to a seventh embodiment of the present invention, the gas supply is a primary gas supply, and the apparatus for controlling a flow of gas from a gas supply to a patient also includes:

One) an auxiliary gas supply;

Two) a selector valve for selecting between a gas flow from the primary gas supply and from the auxiliary gas supply; and Three) detector apparatus for detecting a failure of the flow of gas to the patient from the primary gas supply and for producing a failure signal indicative thereof.

According to a variation of the seventh embodiment of the present invention, the detector apparatus for detecting a failure of the gas flow to the patient from the primary gas supply includes a measuring device for measuring the flow of gas from the primary gas supply. Consequent to a reduction in the flow of gas from the primary gas supply below a predetermined flow, the measuring device produces the failure signal indicative thereof.

According to another variation of the seventh embodiment of the present invention, the selector valve is operable so as to select a gas flow from either the primary gas supply or the auxiliary gas supply. The selector valve operates to select a flow of gas from the auxiliary gas supply in response to the failure signal produced by the detector apparatus.

According to an eighth embodiment of the present invention, the sensor is either an invasive or a non-invasive measuring device.

According to a ninth embodiment of the present invention, the sensor includes apparatus for measuring dissolved oxygen in a blood stream.

In accordance with a further preferred embodiment of the present invention there is provided a program storage device readable by machine, tangibly embodying a program of instructions executable by the machine to perform method steps for controlling a flow of gas from a gas supply to a patient, the method steps include:

One) providing a regulated flow of a predetermined gas from a gas supply to a patient so as to increase the concentration in the patient's bloodstream of a preselected dissolved substance;

Two) measuring the concentration of the preselected dissolved substance in the patient's bloodstream;

Three) producing an output signal indicative of the measured concentration; and

Five) comparing the measured concentration of the preselected dissolved substance with a desired concentration thereof, so as to determine sufficiency of the regulated flow of the predetermined gas to the patient, and adjusting the regulated flow in accordance therewith.

BRIEF DESCRIPTION OF THE DRAWINGS

The present invention will be more fully understood and its features and advantages will become apparent to those skilled in the art by reference to the ensuing description, taken in conjunction with the accompanying drawings, in which.

DETAILED DESCRIPTION OF THE INVENTION

Figure 1:
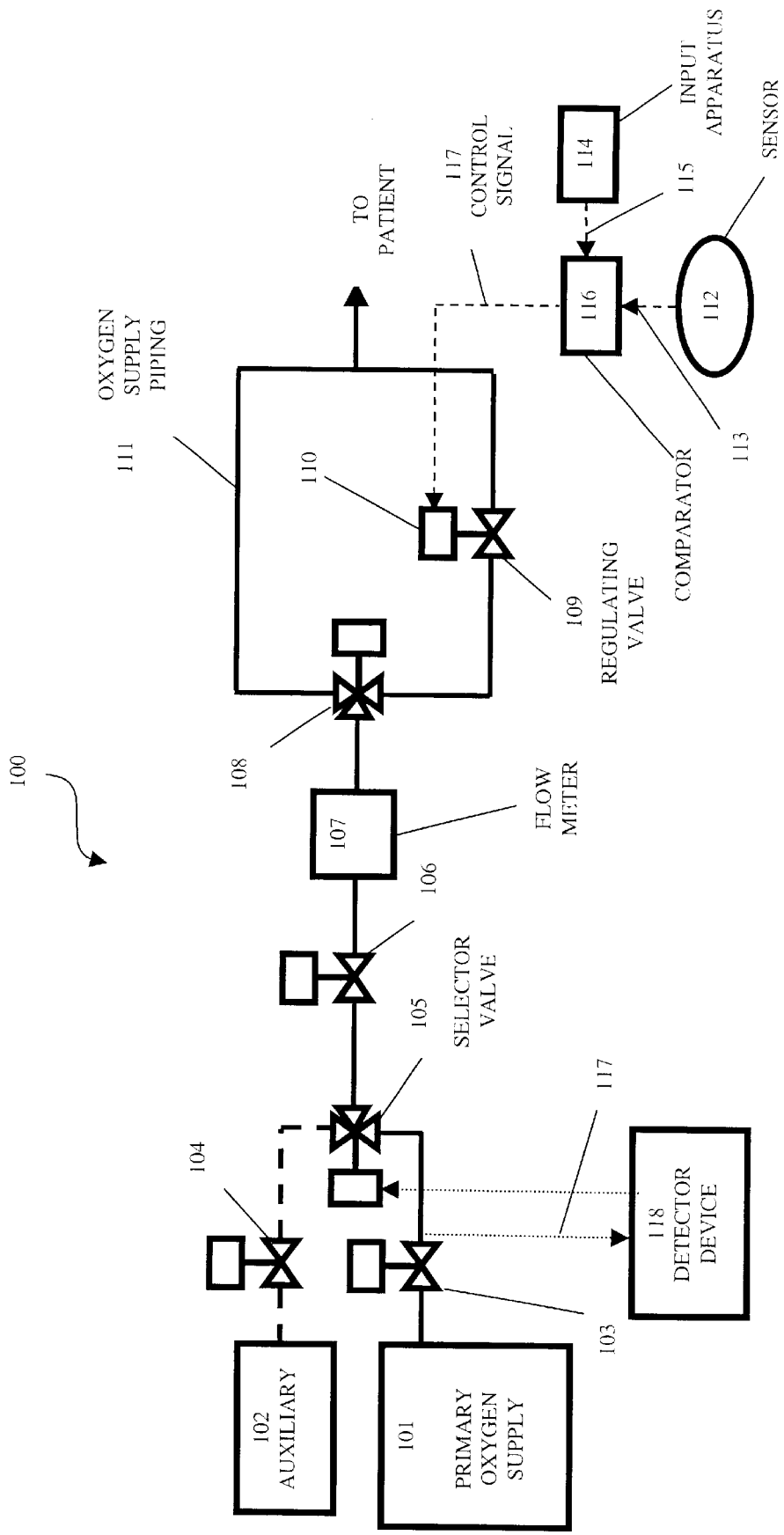
FIG. 1 is a block diagram representation of apparatus for controlling a flow of oxygen containing gas from a gas supply to a patient, constructed and operative in accordance with a preferred embodiment of the present invention.

Referring now to FIG. 1, there is provided apparatus generally referred to as 100 for automatically controlling a flow of oxygen or oxygen containing gas from a primary oxygen supply 101 or from an auxiliary oxygen supply 102 to a patient. Apparatus 100 is constructed and operative in accordance with a preferred embodiment of the present invention.

In order to give effect to the control of the flow of oxygen to a patient, apparatus 100 includes a sensor 112 which is affixed to the patient, for measuring the blood oxygen level in a patient's bloodstream. Sensor 112 sends an output signal 113 to a comparator 116. A selected desired oxygen level in a particular patient's bloodstream is entered into an input apparatus 114, which, in turn, sends an equivalent input signal 115 to comparator 116. The comparator 116 operates to compare the patient's measured blood oxygen concentration, obtained from sensor 112, and the selected desired blood oxygen level obtained from input apparatus 114. Thereafter, comparator 116 delivers a regulating signal 117 to a regulating valve 109, which includes a regulating valve motor 110. In response to this regulating signal 117, regulating valve motor 110 adjusts the regulating valve 109 orifice to cause a suitable flow of gas appropriate to the measurement of blood oxygen and, therefore, to the needs of the patient.

Apparatus 100 further includes a primary oxygen supply 101 feeding oxygen via oxygen supply piping 111 through a primary supply valve 103 to one inlet port of a two-way selector valve 105. Connected to the other inlet port of selector valve 105 are auxiliary oxygen supply 102 and supply valve 104. From selector valve 105 outlet port, gas passes through manual control valve 106 and through gas flow meter 107 which indicates the actual gas rate. Manual control valve 106 is ordinarily left fully open during normal operation of this system and is only required for emergency manual use. From flow meter 107, gas passes into an inlet port of two-way valve 108. During normal system operation, this two-way valve 108 directs the flow of gas via one outlet port to a regulating valve 109 and thereafter to the patient. Only in emergency situations will gas be directed to the patient from the alternative outlet port of two-way valve 108.

The auxiliary oxygen supply 102 is provided so that, should there be a failure of supply from the primary oxygen supply 101, a patient will continue to be supplied with oxygen. To give effect to continuous supply, relating to a flow failure from primary supply 101, auxiliary supply signal 117 is received by detector device 118, which, in turn, causes opening of selector valve 105 auxiliary supply port, to permit gas flow from auxiliary oxygen supply 102.

Figure 2:
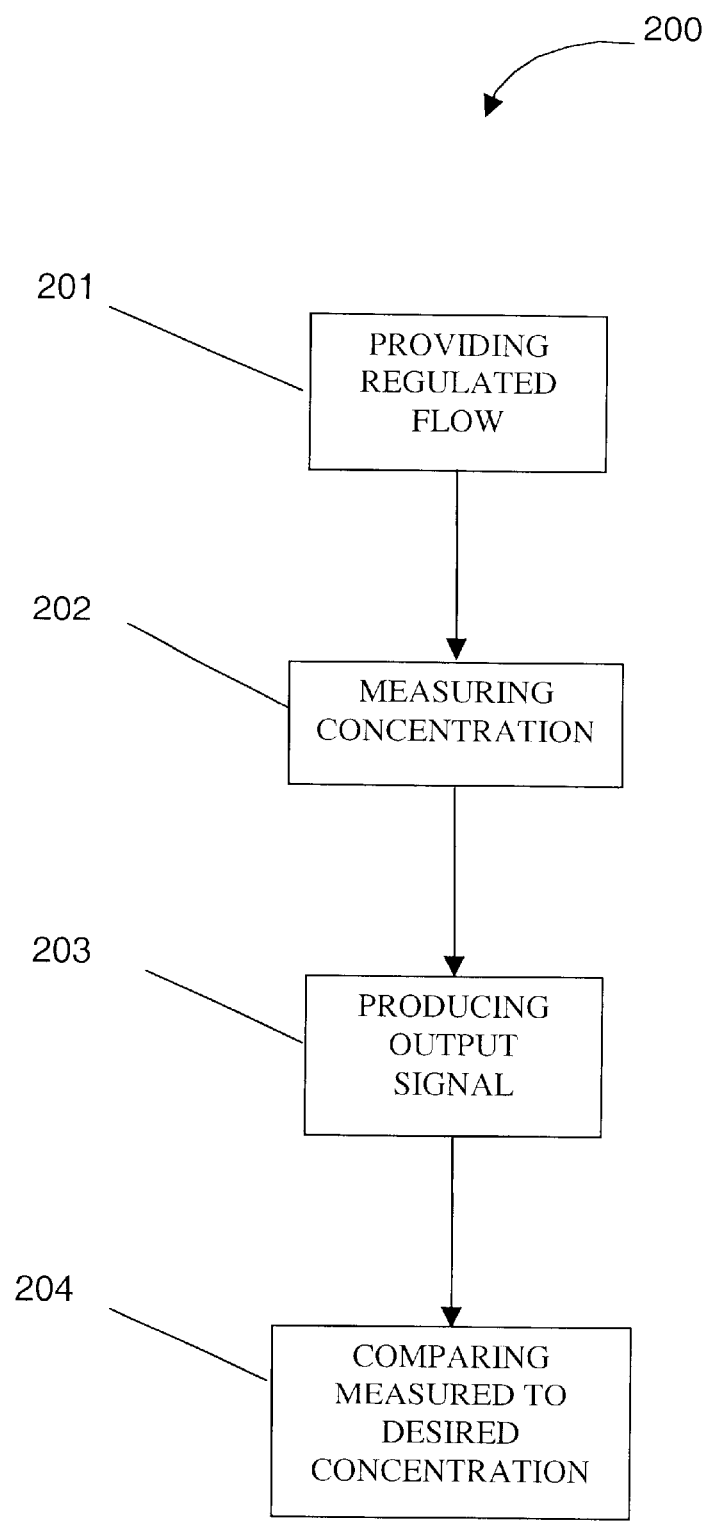
FIG. 2 is a flow chart representation of a method for controlling a flow of a predetermined gas from a gas supply to a patient.

Referring now to FIG. 2, there is provided a representation of a method generally referred to as 200 for controlling a flow of a predetermined gas from a gas supply to a patient.

The present invention relates to a method for controlling a flow of gas from a gas supply to a patient, the method including the following steps:

One) providing 201 a regulated flow of a predetermined gas from a gas supply to a patient so as to increase the concentration in the patient's bloodstream of a preselected dissolved substance;

Two) measuring 202 the concentration of the preselected dissolved substance in the patient's bloodstream;

Three) producing 203 an output signal indicative of the measured concentration; and Four) comparing 204 the measured concentration of the preselected dissolved substance with a desired concentration thereof, so as to determine sufficiency of the regulated flow of the predetermined gas to the patient, and adjusting the regulated flow in accordance therewith.

During the process of causing a gas flow to a patient from a gas supply, there exists the possibility of a supply failure and thereupon the need for initiating an auxiliary supply. As soon as a gas supply failure is detected, a flow of gas is initiated from the auxiliary supply. Failure is either a fall in flow rate below a predetermined rate or a total cessation of flow. That this step is automatically facilitated, makes it much easier for patients who are physically infirm or disabled and would otherwise require assistance to change to an auxiliary supply.

In order to provide a controlled regulation of gas flow to a patient, it is necessary to provide a signal related to a measure of the concentration of a dissolved substance in the bloodstream and to compare this with a desired concentration specified by a medical professional. The flow of gas is then adjusted automatically in accordance with this comparison.

The preselected dissolved substance is generally oxygen, although there are circumstances when other dissolved substance, such as, for example, carbon dioxide, carbon monoxide and others, need to be monitored prior to and during oxygen therapy.

The maximum and minimum concentration of the dissolved substance, usually oxygen, is selected at the outset of therapy by an attending medical professional. Should these preset concentrations or levels prove unsatisfactory, changes can be made as required.

Various methods of oxygen supply are commonly used. These include liquefied oxygen generally stored in a central supply tank and piped to each ward in a hospital type environment. Relatively more portable are various sizes of high-pressure metal cylinders of compressed oxygen. Portable oxygen concentrators supply air from which much of the nitrogen has been removed leaving a high proportion of oxygen.

Figure 3:
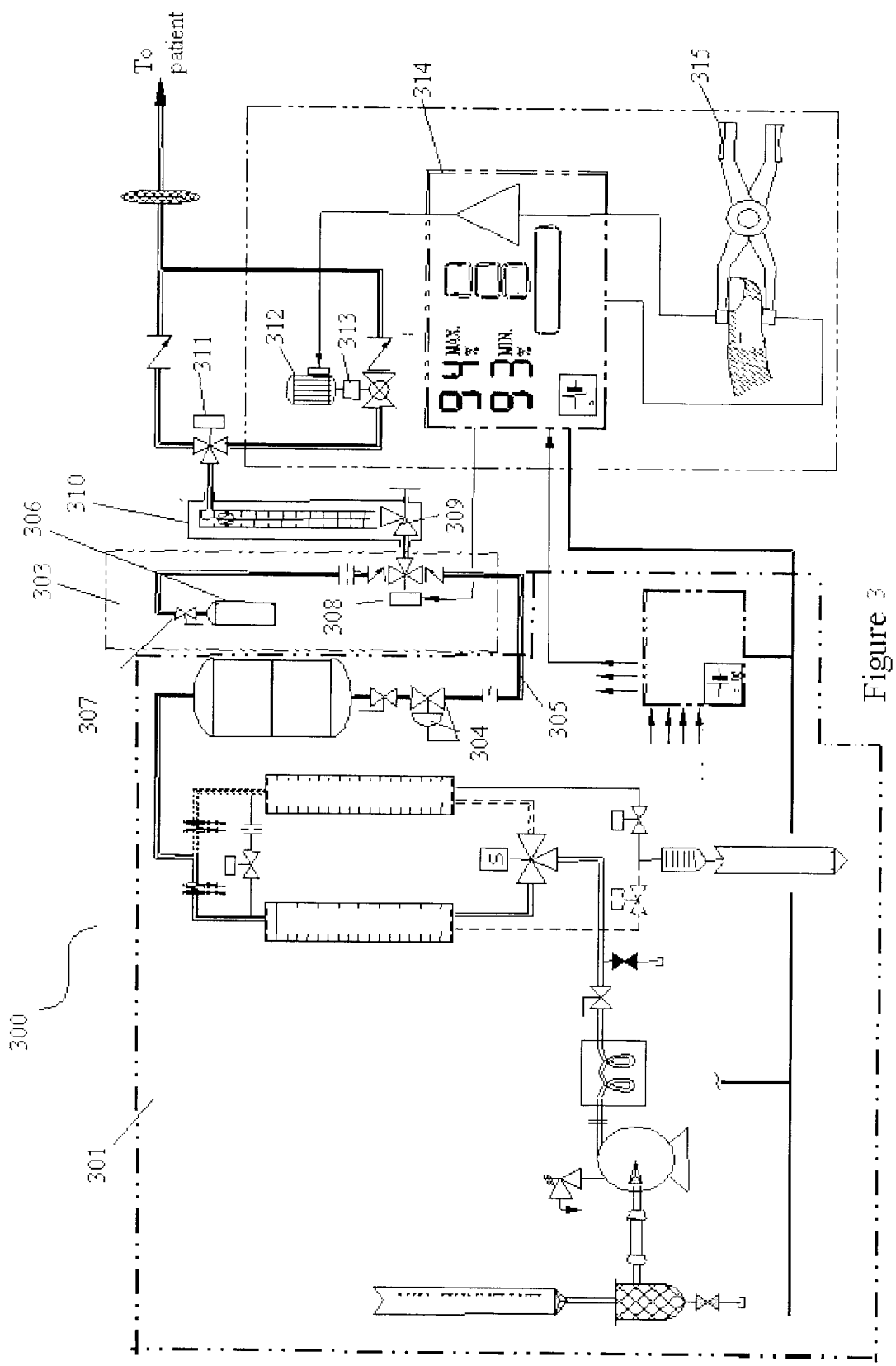
FIG. 3 is a more detailed diagrammatic representation of the apparatus depicted in FIG. 1 in accordance with a preferred embodiment of the present invention.

Referring now to FIG. 3, this is a more detailed diagrammatic representation of an apparatus, generally referred to as 300, compared to that depicted in FIG. 1 in accordance with a preferred embodiment of the present invention.

The gas supply 301 shown is an oxygen generator, which produces an oxygen containing gas by reducing the nitrogen content of air using an adsorption process. Oxygen leaves a storage vessel via valve 304 and piping 305 and enters one port of two-way selector valve 308.

An auxiliary oxygen supply system 303 includes auxiliary oxygen supply container 306 and shut-off valve 307, which supplies gas to the other inlet port of selector valve 308. In the event of a failure of supply from primary supply 301, a detector device, in this instance, incorporated into control device 314, initiates a change of selection to selector valve 308 and permits the flow of oxygen from auxiliary supply 303.

The gas then passes through a manual valve 309, normally left open except in emergencies, and passes through a flow meter 310 into the inlet port of a two-way valve 311. Gas normally passes through one exit port of two-way valve 311, to a regulating valve 313, which generally includes a control mechanism such as a servomotor 312. A regulating signal adjusts the regulating valve 313 and thereby the flow of gas to the patient.

To produce this regulating signal, a desired oxygen level is set on the input apparatus, incorporated, in this schematic view, with the control device 314. Further, an oxygen-measuring device or sensor 315 generates a signal relative to the blood oxygen level. Together with the input signal related to the desired oxygen level, the signal relating to the measured oxygen level passes into a comparator, also incorporated into control device 314, in this view. The comparator produces a regulating signal, which causes regulating valve 313 to adjust the gas flow to the patient.

Returning to FIG. 2, the present invention further relates to a program storage device readable by machine, tangibly embodying a program of instructions executable by the machine to perform method 200 steps for controlling a flow of gas from a gas supply to a patient, the method steps including:

One) providing 201 a regulated flow of a predetermined gas from a gas supply to a patient so as to increase the concentration in the patient's bloodstream of a preselected dissolved substance;

Two) measuring 202 the concentration of the preselected dissolved substance in the patient's bloodstream;

Three) producing 203 an output signal indicative of the measured concentration; and Four) comparing 204 the measured concentration of the preselected dissolved substance with a desired concentration thereof, so as to determine sufficiency of the regulated flow of the predetermined gas to the patient, and adjusting the regulated flow in accordance therewith.

It will be appreciated by persons skilled in the art that the present invention is not to be limited by the drawings and description hereinabove presented. Rather, the invention is defined solely by the claims which follow.

What is claimed is:

1. A method for controlling a flow of gas from a gas supply to a patient, the method including the following steps:
    a) providing a regulated flow of a predetermined gas from a gas supply to a patient so as to increase the concentration in the patient's bloodstream of a preselected dissolved substance;
    b) measuring the concentration of the preselected dissolved substance in the patient's bloodstream;
    c) producing an output signal indicative of the measured concentration; and
    d) comparing the measured concentration of the preselected dissolved substance with a desired concentration thereof, so as to determine sufficiency of the regulated flow of the predetermined gas to the patient, and adjusting the regulated flow in accordance therewith said method also including, in response to a failure of said providing step, the additional step of initiating a flow of a predetermined gas from an auxiliary gas supply, thereby to maintain a flow of gas to the patient.

2. A method according to claim 1, wherein said additional step of initiating a flow of gas includes the sub-step of detecting a failure of the regulated gas flow from the gas supply below a predetermined gas flow.

3. A method according to claim 1, wherein in said additional step of initiating a flow of gas from an auxiliary gas supply, the gas from the auxiliary supply contains oxygen.

4. A method according to claim 1, wherein in said additional step of initiating a flow of gas from an auxiliary gas supply, the gas from the auxiliary supply is substantially oxygen.

5. A method for controlling a flow of gas from a gas supply to a patient, the method including the following steps:
    a) providing a regulated flow of a predetermined gas from a gas supply to a patient so as to increase the concentration in the patient's bloodstream of a preselected dissolved substance;
    b) measuring the concentration of the preselected dissolved substance in the patient's bloodstream;
    c) producing an output signal indicative of the measured concentration; and
    d) comparing the measured concentration of the preselected dissolved substance with a desired concentration thereof, so as to determine sufficiency of the regulated flow of the predetermined gas to the patient, and adjusting the regulated flow in accordance therewith, and wherein, in said steps a) of providing a regulated flow of a predetermined gas from a gas supply to a patient so as to increase the concentration in the patient's bloodstream of a preselected dissolved substance and b) of measuring a concentration of the preselected dissolved substance, the preselected dissolved substance is oxygen.

6. Apparatus for controlling a flow of gas from a gas supply to a patient, wherein said apparatus includes:
    a) a regulating valve arranged in association with a gas supply, for regulating a flow of gas therefrom to a patient in response to predetermined control signals;
    b) a sensor for measuring a concentration of a preselected dissolved substance in the blood stream of the patient and for providing an output signal indicative of the concentration of the measured substance;
    c) input apparatus for inputting a desired concentration of the dissolved substance in the patient's bloodstream; and
    d) comparator apparatus associated with said automatic regulating valve, said sensor and said input apparatus, operative to compare a measured concentration with the desired concentration so as to determine sufficiency of the regulated flow of the predetermined gas to the patient, and so as to provide to said regulating valve a control signal so as to adjust said regulating valve in accordance with the determined sufficiency of the regulated flow, and wherein the gas supply is a primary gas supply, and wherein said apparatus for controlling a flow of gas from a gas supply to a patient also includes:
    a) an auxiliary gas supply;
    b) a selector valve for selecting between a gas flow from the primary gas supply and a gas flow from said auxiliary gas supply; and.
    c) detector apparatus for detecting a failure of the flow of gas to the patient from the primary gas supply and for producing a failure signal indicative thereof.

7. Apparatus according to claim 6, wherein said detector apparatus for detecting a failure of the gas flow to the patient from the primary gas supply includes a measuring device for measuring the flow of gas from the primary gas supply and, consequent to a reduction in the flow of gas from the primary gas supply below a predetermined flow, for producing the failure signal indicative thereof.

8. Apparatus according to claim 6, wherein said selector valve for selecting between a gas flow to the patient from the primary gas supply and from said auxiliary gas supply, is operative to select a flow of gas from said auxiliary gas supply in response to the failure signal produced by said detector apparatus.

9. A program storage device readable by machine, tangibly embodying a program of instructions executable by the machine to perform method steps for controlling a flow of gas from a gas supply to a patient, the method steps including:
    a) providing a regulated flow of a predetermined gas from a gas supply to a patient so as to increase the concentration in the patient's bloodstream of a preselected dissolved substance;
    b) measuring the concentration of the preselected dissolved substance in the patient's bloodstream;
    c) producing an output signal indicative of the measured concentration; and
    d) comparing the measured concentration of the preselected dissolved substance with a desired concentration thereof, so as to determine sufficiency of the regulated flow of the predetermined gas to the patient, and adjusting the regulated flow in accordance therewith, and wherein the method steps further include, in response to a failure of said step a) of providing a regulated flow, the additional step of initiating a flow of a predetermined gas from an auxiliary gas supply, thereby to maintain a flow of gas to the patient.

10. The program storage device readable by machine according to claim 9, wherein the method steps further include, the sub-step of detecting a failure of the regulated gas flow from the gas supply below a predetermined gas flow.

11. The program storage device readable by machine, according to claim 9 wherein, in said steps a) of providing a regulated flow of a predetermined gas from a gas supply to a patient so as to increase the concentration in the patient's bloodstream of a preselected dissolved substance and b) of measuring a concentration of the preselected dissolved substance, the preselected dissolved substance is oxygen.

12. The program storage device readable by machine according to claim 9, wherein in the additional step of initiating a flow of gas from an auxiliary gas supply, the gas from the auxiliary supply contains oxygen.

13. The program storage device readable by machine according to claim 9, wherein in the additional step of initiating a flow of gas from an auxiliary gas supply, the gas from the auxiliary supply is substantially oxygen.

14. The program storage device readable by machine according to claim 9, wherein the method steps further include, the additional step of assigning, prior to said step b) of measuring, at least one of the following:
   a) a maximum desired concentration of the preselected dissolved substance in the patient's bloodstream; and
   b) a minimum desired concentration of the preselected dissolved substance in the patient's bloodstream.

* * * * *